United States Patent
Cavallaro et al.

(10) Patent No.: US 7,051,600 B1
(45) Date of Patent: May 30, 2006

(54) TRIAXIAL TENSION COMPRESSION, SHEAR TESTING APPARATUS

(75) Inventors: Paul V. Cavallaro, Raynham, MA (US); Ali M. Sadegh, Franklin, NJ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/905,076

(22) Filed: Dec. 14, 2004

Related U.S. Application Data

(63) Continuation-in-part of application No. 10/851,748, filed on May 24, 2004, now Pat. No. 6,860,156.

(51) Int. Cl.
*G01D 7/00* (2006.01)
(52) U.S. Cl. ................................. 73/862.041
(58) Field of Classification Search ............... None
See application file for complete search history.

(56) References Cited

U.S. PATENT DOCUMENTS

| | | | |
|---|---|---|---|
| 1,496,803 A | | 6/1924 | Amsler |
| 3,776,028 A | | 12/1973 | Lynch et al. |
| 4,192,194 A | | 3/1980 | Holt |
| 4,677,854 A | | 7/1987 | Gabelli |
| 4,885,941 A | | 12/1989 | Vardoulakis et al. |
| 5,144,844 A | | 9/1992 | Mathiak et al. |
| 5,279,166 A | | 1/1994 | Ward et al. |
| 5,336,854 A | * | 8/1994 | Johnson .............. 177/210 FP |
| 5,448,918 A | | 9/1995 | Tucchio |
| 5,651,229 A | * | 7/1997 | Wada et al. ................ 52/693 |
| 5,798,463 A | | 8/1998 | Doudican et al. |
| 5,905,205 A | | 5/1999 | Clay |
| 6,058,784 A | | 5/2000 | Carroll et al. |
| 6,487,902 B1 | | 12/2002 | Ghosh |
| 6,532,830 B1 | * | 3/2003 | Jansen et al. .......... 73/862.042 |
| 6,860,156 B1 | * | 3/2005 | Cavallaro et al. ............. 73/819 |

* cited by examiner

OTHER PUBLICATIONS

W.Denney Fresston, Jr. et al., Mechanics of Elastic Performance of Textile Materials, Part XVIII, Stress-Strain Response of Fabric Under Two-Dimensional Loading, Manuscript, Nov. 1967, pp. 948-975, Textile Research Journal, USA.

*Primary Examiner*—Max Noori
*Assistant Examiner*—Octavia Davis
(74) *Attorney, Agent, or Firm*—Michael P. Stanley; James M. Kasischke; Jean-Paul A. Nasser

(57) ABSTRACT

A triaxial testing system of material properties having top and bottom joint assemblies that rotate about and move along a longitudinal axis in response to forces imparted by a testing machine. The joint assemblies are connected together by horizontal and vertical linkage assemblies. The horizontal and vertical linkage assemblies are connected to horizontal and vertical loading and clamping assemblies to thereby transfer in-plane and multi-axial loads from the testing machine and the joint assemblies to a material test specimen. The test specimen is rigidly clamped to the horizontal and vertical clamping assemblies. The bases and ends of the test specimen are shaped for clamping and axial loading. Rigid plates may be disposed over ends of composite test specimens for spatially stabilizing such specimens during testing. The test specimens may include devices to measure and record the axial and shear loads, displacement and strains imparted to the specimens during testing.

12 Claims, 9 Drawing Sheets

TRIAXIAL TENSION COMPRESSION, SHEAR TESTING APPARATUS

CROSS-REFERENCE TO RELATED APPLICATIONS

This application is a continuation-in-part of and claims the benefit of U.S. patent application (Ser. No. 10/851,748—filed on May 24, 2004 now U.S. Pat. No. 6,860,156 and allowed on Oct. 20, 2004), entitled "Combined In-Plane Shear and Multi-Axial Tension or Compression Testing".

STATEMENT REGARDING FEDERALLY SPONSERED RESEARCH OR DEVELOPMENT

The invention described herein may be manufactured and used by and for the Government of the United States of America for governmental purposes without the payment of any royalties thereon or therefore.

(1) FIELD OF THE INVENTION

The present invention relates to a system for testing the material properties of physical specimens, more particularly to an apparatus and process for determining the mechanical properties of metals, plastics, woods, fabrics, elastomers and composites of similar materials in response to multi-axial and shear loads imparted to test specimens of such materials by the apparatus of the system.

(2) DESCRIPTION OF THE PRIOR ART

Plain-woven fabrics are widely utilized as structural materials in air-inflated structures and rapidly deployable structures such as temporary shelters, tents, temporary bridges and space structures. Unlike metallic structures, these structures are primarily designed to be lightweight, self-erecting and deployable to volume-storage ratios that may be 1000-to-1. Air-inflated structures utilize pressurized fabric tubes and pressure-stabilized beams (known as air beams) as load-carrying members.

Although, such structures are well known in the art, the technology for the structures has not been refined such that reliable structures can be analytically designed. Specifically, this analysis has gained in importance due to advancements in the material of the structural fiber and the weaving/braiding of the structural fiber, both of which have improved the load carrying capacity of the structures. Accordingly, there is a recognized need to model the mechanical properties of woven fabrics.

Presently, modeling the mechanical properties of woven fabrics results in complex responses because of the complex microstructures of the composite materials used. Unlike traditional composite materials, plain-woven fabrics used in inflated structures exhibit high non-linearity with a dependence on internal pressure and contact interactions within the woven fabric. Accordingly, there is a need for a testing apparatus that measures the elastic and shear moduli of air beams as a function of inflation pressure.

To measure the elastic modulus of the fabric, a multi-axial loading has been shown to be preferable and to measure the shear moduli of the fabric; an in-plane shear loading has been shown to be preferable. As such, there is a need for a testing apparatus capable of combining multi-plane shear and multi-axial loading. For non-orthogonal composite or fabric materials, such as braids or knits, there is a further need for a testing apparatus capable of loading the specimen in varying orthogonal positions.

While biaxial testing apparatuses with compression and tension loading or in-plane shear testing apparatuses exist in the prior art, there are no apparatuses that exist with a combined feature of multi-plane shear and triaxial testing capabilities.

Additionally, testing apparatuses of the prior art employ two or more separate actuators in complex test fixtures or pressurization techniques for applying a biaxial load to a test specimen. An apparent disadvantage is the need for two or more loading devices and the associated high cost of equipment.

In regard to specific references, Lynch et al. (U.S. Pat. No. 3,776,028) describes an apparatus requiring three independent loading mechanisms. Holt (U.S. Pat. No. 4,192,194) describes an apparatus for biaxial loading of a specimen by pressurizing the inside surface of a cylinder. A restrictive disadvantage of the apparatus is the requirement of the cylindrical shape of the specimen and a high cost associated with pressurization of the cylinder. Additionally, the disadvantages include restriction to orthogonal loads about the axial, hoop and radial directions and an apparatus that is not capable of applying an in-plane shear stress to the specimen.

Mathiak et al. (U.S. Pat. No. 5,144,844) describes a cruciform planar specimen for biaxial material testing which has the disadvantage of being limited to use in two loading directions. Ward et al. (U.S. Pat. No. 5,279,166) describes an apparatus for self-alignment of a biaxial loading device. The apparatus requires that the two axial loading directions be orthogonal with a maximum of two loading directions. The apparatus also has no capability for applying an in-plane shear load to the specimen.

Tucchio (U.S. Pat. No. 5,448,918) describes an apparatus with an X-shape that is only used for compression load. Clay (U.S. Pat. No. 5,905,205) describes an in-plane biaxial test apparatus comprising linkages to transfer the load to an orthogonal direction of loading. A disadvantage of this apparatus is that it is not capable of applying in-plane shear to the test specimen. Another disadvantage of this apparatus is that the biaxial loading is limited to an orthogonal configuration.

As noted above, none of the references are capable of combining the in-plane and multi-axial loading of a specimen while only using one loading system. As such, there exists a need for an apparatus capable of applying a combined in-plane shear and multi axial loads to a test specimen. Such an apparatus would be cost-effective due to reduced space and a reduced amount of equipment normally needed for material testing.

BRIEF SUMMARY OF THE INVENTION

The present invention is directed to a material properties testing system that satisfies the need for a need for a system capable of applying combined in-plane shear and multi axial loads to a test specimen. The present invention is further directed to providing a single material testing system that is compact, cost-effective and easy to assemble and disassemble. The apparatus of the present system includes a triaxial test specimen that is configured to facilitate the triaxial testing of solid and composite specimens.

Therefore, an object of the present invention is to provide a triaxial testing apparatus that is capable of applying combined in-plane shear and multi-axial loads to a test specimen.

A further object of the present invention single material testing apparatus that is compact, cost-effective and easy to assemble and disassemble.

Another object of the present invention is to provide test specimens that are configured to accurately and conveniently test the material properties of solid and composite specimens by a triaxial testing apparatus.

According to the present invention, the foregoing and other objects and advantages are attained by an apparatus of the triaxial testing system that has a top and a bottom joint assembly, and where each joint assembly has sleeves capable of rotational movement about and linear movement along a longitudinal axis. The system also includes a plurality of horizontal force members having first and second ends, and where each horizontal force member is connected at the first end to one of the top or bottom joint assemblies and is adapted for receiving the rotational and linear movement of the top and bottom joint assemblies. The apparatus of the system further includes a plurality of horizontal loading assemblies, where each horizontal loading assembly is connected to the second end to the horizontal force members and is adapted for receiving the rotational and linear movement of said horizontal force members and transferring it as axial and shear loading to a test specimen. The apparatus of the system also includes a plurality of vertical force members, where each vertical force member is connected to a sleeve of the top or bottom joint assemblies and is adapted for receiving the rotational and linear movement of the top or bottom joint assemblies. The apparatus of the system includes a plurality of vertical loading assemblies, where each vertical loading assembly is connected to vertical force members for receiving the rotational and linear movement of the vertical force members and transferring it as axial and shear loading to said test specimen.

Another aspect of the apparatus of the present invention is that a plurality of horizontal clamping assemblies are each connected to one of the horizontal loading assemblies and are adapted for horizontally clamping the test specimen. The apparatus of the present invention further includes a plurality of vertical clamping assemblies, where each vertical assembly is connected to one of the vertical loading assemblies and is adapted for vertically clamping the test specimen.

One other aspect of the apparatus of the present invention is that a loading bar is connected to one of the top and bottom joint assemblies and is adapted for holding the vertical loading assembly. The apparatus of the present invention further includes a plurality of rods, each rod connected at one end to the loading bars and adapted for receiving and transferring the rotational and linear movement of the top and bottom joint assemblies to the test specimen.

Yet another aspect of the apparatus of the present invention is a test specimen that includes a plurality of horizontal and vertical ends that are shaped for clamping by the horizontal and vertical clamping assemblies.

Still another aspect of the apparatus of the present invention is that the testing specimen further includes at least one load measurement device for measuring the axial and shear loads imparted to the test specimen by the horizontal and vertical loading assemblies.

An aspect of the apparatus of the present invention is that the test specimen further includes a plurality of rigid plates, where each plate is disposed over one of the horizontal ends for spatially stabilizing specimens made of composite materials.

An additional aspect of the apparatus of the present invention is that at least one crosshead is connected to at least one of the top and bottom joint assemblies for imparting rotational and linear movement to the top and bottom joint assemblies.

Further according to the present invention, the foregoing and other objects and advantages are attained by a process of the triaxial testing system that imparts rotational and linear motion to a top and a bottom joint assembly, that receives the rotational and linear motion from the top and bottom joint assemblies; and that transfers the rotational and linear motion from the top and bottom joint assemblies as axial and shear loading to a test specimen.

An additional aspect of the process of the present invention is that the process of transferring the rotational and linear motion as axial and shear loading further comprises horizontally clamping the test specimen.

Another aspect of the process of the present invention is that the process of transferring the rotational and linear motion as axial and shear loading further comprises vertically clamping the test specimen.

Yet a further aspect of the process of the present invention includes shaping the ends of the test specimen for clamping.

Another aspect of the process of the present invention comprises measuring the axial and shear loads imparted to the test specimen by the top and bottom joint assemblies.

An additional aspect of the process of the present invention includes connecting at least one crosshead to at least one of the top and bottom joint assemblies to thereby impart rotational and linear movement to the top and bottom joint assemblies.

Further according to the present invention, the foregoing and other objects and advantages are attained by a triaxial testing system that includes means for imparting rotational and linear motion to a top and a bottom joint assembly, means for transferring the rotational and linear motion as axial and shear loading to a test specimen; and means for clamping the test specimen.

An additional aspect of the clamping means of the present invention further comprises means for horizontally clamping the test specimen.

Another aspect of the clamping means of the present invention further comprises means for vertically clamping the test specimen.

An aspect of system of the present invention further includes means for shaping the test specimen for clamping.

A further aspect of the system of the present invention further comprises means for spatially stabilizing test specimens made of composite materials.

An aspect of the system of the present invention also includes means for measuring the axial and shear loads imparted to the test specimen by the top and bottom joint assemblies.

Another aspect of the means for imparting rotational and linear movement of the present invention further comprises at least one crosshead connected least one of the top and bottom joint assemblies.

The triaxial testing apparatus of the present invention enables a user to test the material properties of a triaxial test specimen by applying combined in-plane shear and multi-axial loads to the test specimen. In particular, the triaxial test apparatus is configured to expediently transfer forces from a conventional testing machine to a test specimen in the form of horizontal compression, horizontal tension, vertical compression, vertical tension and shear loads, and combinations thereof. The ends of the test specimen of the present invention are adapted for clamping by the horizontal and vertical clamping assemblies. Alternatively, the ends test specimen of the present invention may include rigid plates, where each plate is disposed over one of the horizontal ends of the test specimen for spatially stabilizing specimens made of composite materials during operation of the triaxial testing apparatus. The test specimens may also include load measurement devices that facilitate convenient and accurate measurement of the horizontal, vertical and shear loads imparted to the test specimen by the testing machine during operation of the triaxial testing apparatus.

BRIEF DESCRIPTION OF THE SEVERAL VIEWS OF THE DRAWING

A more complete understanding of an embodiment of the invention and many of the attendant advantages thereto will be readily appreciated as the same becomes better understood by reference to the following detailed description of an embodiment of the invention when considered in conjunction with the accompanying drawings wherein.

DETAILED DESCRIPTION OF THE INVENTION

Figure 1:
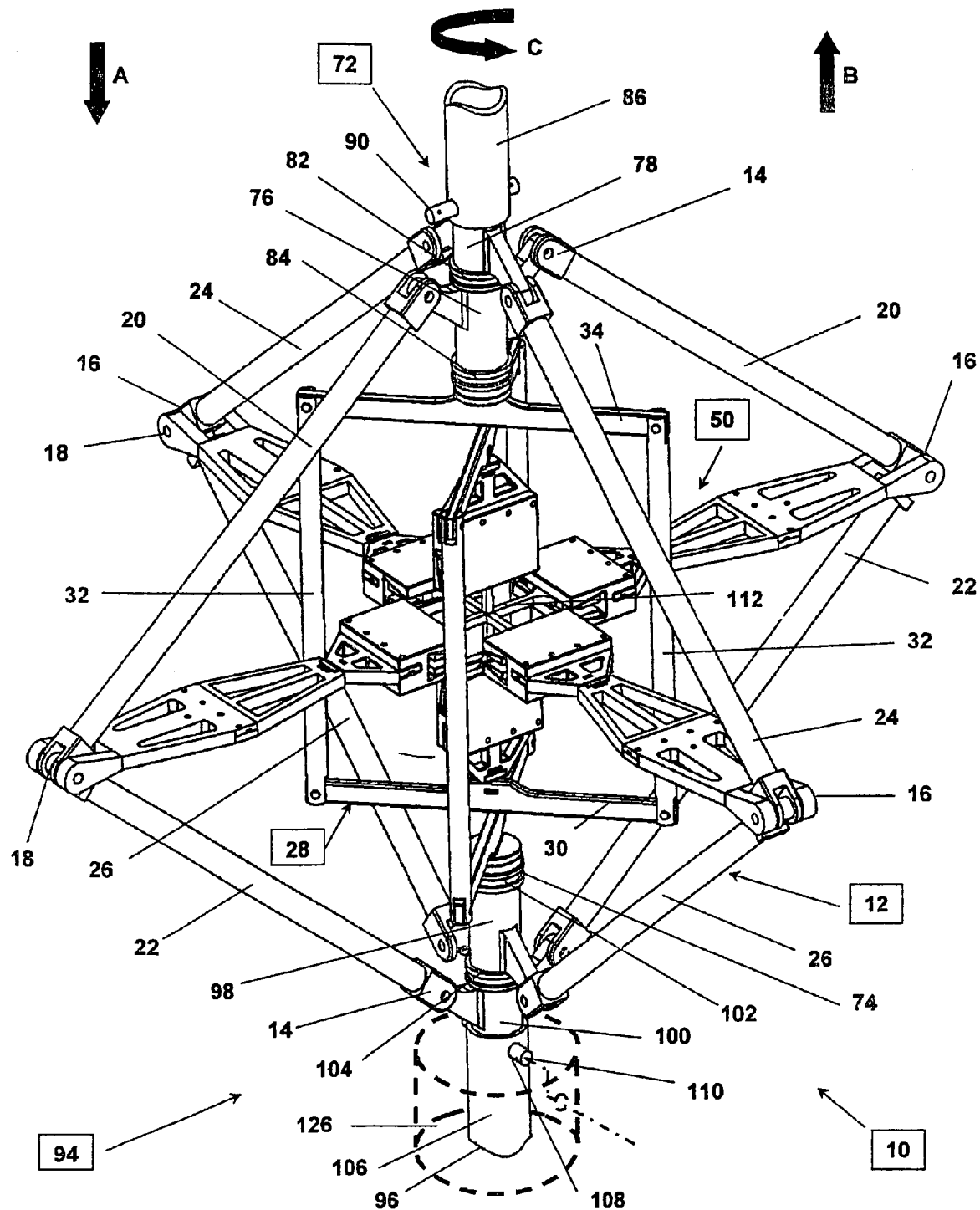
FIG. 1 shows an isometric view of the triaxial testing apparatus in accordance with an embodiment of the invention.

Referring now to Figures (FIGS.) 1–9, wherein like numerals refer to like elements throughout the several views, a triaxial testing apparatus 10 is shown in which the triaxial testing apparatus comprises a plurality of horizontal force members 12 and a vertical loading assembly 28 connected together to top joint assembly 72 and to bottom joint assembly 94. The horizontal force members 12, comprising linkages 20, 22, 24 and 26, are further connected to horizontal loading assembly 50 and to horizontal clamping assembly 64; and are similarly attached to vertical loading assembly 28 and to vertical clamping assembly 38. The horizontal clamping assembly 64 and the vertical clamping assembly 38 function together to rigidly clamp triaxial test specimen 112 in place for material properties testing during operation of the triaxial testing apparatus 10.

The top joint assembly 72 includes first and second sleeves 76, 78, and the bottom joint assembly 94 includes third and fourth sleeves 98, 100, and each of the sleeves are configured to rotate independently of each other about and along a longitudinal axis in proportionate response to force imparted to top crosshead 86 or to bottom crosshead 106 by testing machine 126. The longitudinal and rotational movements of the sleeves 76, 78, 98, 100 of the top and bottom joint assemblies 72, 94 are transferred by the horizontal force members 12 to the horizontal loading assembly 50, and by the vertical loading assembly 28 to loading bar 34. The horizontal loading assembly 50 and the loading bar 34 further impart the longitudinal and rotational axial movement as horizontal compression, horizontal tension, vertical compression, vertical tension and shear loads, and combinations thereof, to the triaxial test specimen 112.

The triaxial test specimen 112 includes load measurement devices 114 for measuring and recording the compression, tensile and shears loads imparted by triaxial testing apparatus 10 to the test specimen during material properties testing.

How to Make an Embodiment of the Invention

Referring further to the isometric view of an embodiment of the invention disclosed in Figure (FIG.) 1, the horizontal force members 12 includes the linkages 20, 22, 24, 26 (hereinafter 20–26), preferably two sets of four linkages each that are connected together to define a perimeter of variable rhombus shape. Each pair of linkages (e.g., 20–22 and 24–26) are connected together at one end by bracket links 16, and each linkage is connected at a second end by bracket links 14 to one of the first, second, third or fourth sleeves 76, 78, 98 or 100. A bracket pin 18 is disposed within each of bracket links 14, 16 and functions to enable the linkages 20–26 to pivot in relation to each other and in relation to the top and bottom joint assemblies 72, 94. Preferably, the bracket pin 18 is conveniently removable by the user to facilitate convenient maintenance, assembly and disassembly of triaxial testing apparatus 10. Those skilled in the art will appreciate that the bracket links 14, 16 and the bracket pin 18 may be replaced by any other conventional mechanical fastener that will enable the linkages 20–26 to pivot in relation to each other and in relation to the top and bottom joint assemblies 72, 94.

The bracket pins 18 also function to connect the horizontal loading assembly 50 to the linkages 20–26, and how to make to horizontal loading assembly is disclosed below in reference to FIG. 3. In continued reference to FIG. 1, the triaxial testing apparatus 10 also includes the vertical loading assembly 28 comprising attachment bar 30 and the loading bar 34 connected together at each end by rods 32. The attachment bar 30, the loading bar 34 and the rods 32 together define a perimeter of a variable rhombus shape, similar to the variable rhombus shape of linkages 20–26 disclosed above. The horizontal and vertical loading assemblies 50, 28 function together to transfer compression, tension and shear loads from the top and bottom joint assemblies 72, 94 to the triaxial test specimen 112.

As disclosed above, FIG. 1 shows that the linkages 20–26 are connected at a second end by bracket links 14 to one of top or bottom sleeves 76, 78, 98 or 100. The top joint assembly 72 has the first sleeve 76 and the second sleeve 78 disposed adjacent to each and operable to independently rotate about and along their common longitudinal axes. The top crosshead 86 is disposed adjacent to the first sleeve 76 and engages the top sleeve by action on top pin 90. The first and second thrust bearings 82, 84 are disposed adjacent to each of the first and second sleeves 76, 78 and together with the top crosshead 86 restrain the first and second sleeves 76 and 78 in any direction of movement except for rotation about and along a common longitudinal axis.

In further reference to FIG. 1, the triaxial testing apparatus 10 also includes the bottom joint assembly 94 that has the third sleeve 98 and the fourth sleeve 100 disposed adjacent to each and operable to independently rotate about and along their common longitudinal axes. The bottom crosshead 106 is disposed adjacent to the fourth sleeve 100 and engages the fourth sleeve by action on bottom pin 110. The bottom crosshead 106 rotates about and along a longitudinal axis in response to force imparted to it by the testing machine 126 that is rigidly connected to the bottom pin 110. The bottom pin 110 directly imparts the force to the third and fourth sleeves 98, 100 and third and fourth thrust bearings 102, 104 are disposed adjacent to each of the third and fourth sleeves to restrain the direction of movement of the third and fourth sleeves 98, 100 in response to the force to rotation about and along a common longitudinal axis.

As disclosed above, FIG. 1 shows that the bracket pin 18 is disposed within each of the bracket links 14 and FIG. 1 illustrates that the force imparted by the testing machine to the bottom pin 110 (or to the top pin 90), is transferred to the third and fourth sleeves 98, 100, to the bracket links 14, to linkages 20–26, thence to the horizontal and vertical loading assemblies 50, 28 and thereby transfers horizontal compression, horizontal tension and shear loads from the top and bottom joint assemblies 72, 94 to the triaxial test specimen 112. Similarly, force imparted by the testing machine 126 is imparted to the vertical loading assembly 28, directly to the vertical clamping assembly 38, and thereby transfers vertical compression, vertical tension and shear load from the top and bottom joint assemblies 72, 94 to the triaxial test specimen 112. FIG. 1 also discloses that the top and bottom joint assemblies 72, 94 are connected to each other by linkages 20–26, and that the linkages are connected together in pairs by the bracket links 16. Thus, the triaxial testing apparatus 10 is configured to impart multi-axial loads (horizontal, vertical, and shear loads) to the triaxial test specimen 112.

Finally in reference to FIG. 1, the various parts of triaxial testing apparatus 10 may be made of any suitable structural material that may be manufactured into extruded shapes, plates and pins, and so forth by conventional machining, molding, forging and the like so as to provide a material properties testing apparatus that has high structural strength, high structural stiffness and minimal weight. Preferably, such structural materials include metals, plastics, composites and ceramics known to those skilled in the art and chosen to meet the desired strength, stiffness and lightweight criteria disclosed above. Ceramics, for example, may be used to make parts of the triaxial testing apparatus 10 that may be subjected to very high ambient temperature during use. The extruded shapes include cylindrical tubing for the linkages 20–26, however those skilled in the art will realized that any closed cross-section (e.g., rectangular, square) may be used for the linkages, even solid cross-sectional materials.

The top and bottom joint assemblies 72, 94 may be any shape necessary for strength and durability, however, the shapes of the joint assemblies must enable unrestricted rotational and linear motion of the linkages 20–26, with or without the use of the thrust bearings 82, 84, 102, 104. Further, and alternatively to the bracket pin 18, the linkages 20–26 may be connected to the bracket links 14, 16 by welding, bonding or fastening, or combination of these methods, as necessary to ensure the structural cooperation of the linkages with the top and bottom joint assemblies 72, 94 during operation of the triaxial test apparatus 10.

Figure 2:
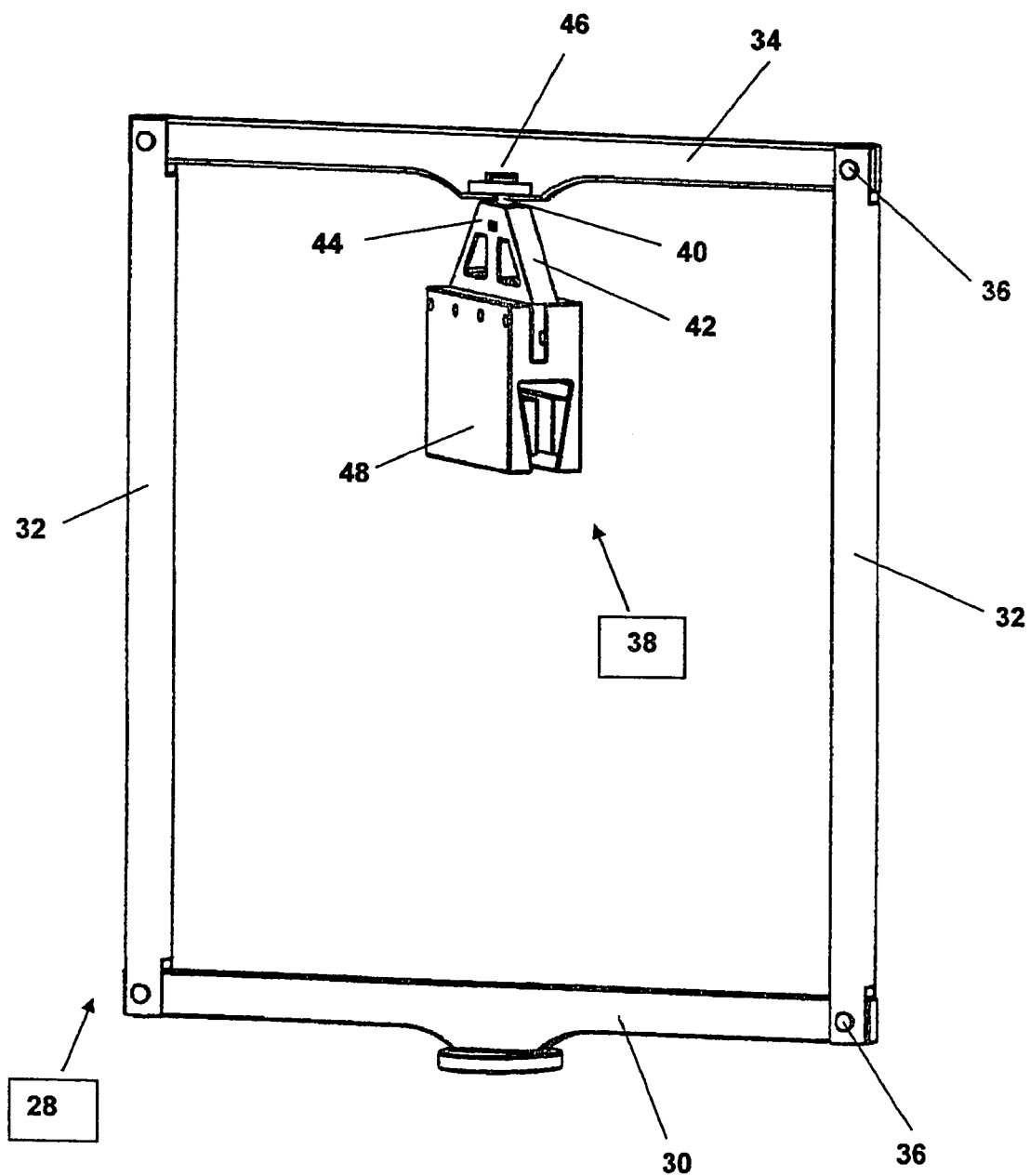
FIG. 2 shows a front view of a vertical loading assembly in accordance with an embodiment of the apparatus of present invention.

FIG. 2 shows a front view of the vertical loading assembly 28, and of the vertical clamping assembly 38, of an embodiment of the present invention. The vertical loading assembly 28 comprises at least two of the rods 32 that are each connected at one end to the attachment bar 30, and connected at another end to the loading bar 34. The rods 32 are connected to the attachment bar 30 and the loading bar 34 by bar pins 36, and the pins also function to enable the rods 32 to pivot in relation to each other and in relation to the attachment bar 30 and the loading bar 34. Preferably, the bar pins 36 are conveniently removable by the user to facilitate maintenance, assembly and disassembly of the vertical loading assembly 28. Those skilled in the art will appreciate that the bar pins 36 may be replaced by any other conventional mechanical fastener the will enable the rods 32, the attachment bar 30 and the loading bar 34 to pivot in relation to each other.

As disclosed above, the vertical loading assembly 28, comprising the attachment bar 30, the loading bar 34 and the rods 28 together define a perimeter of variable rhombus shape, similar to the variable rhombus shape of the linkages 20–26, also disclosed above. The vertical loading assembly 28 functions to transfer vertical compression, vertical tension and shear loads from the top and bottom joint assemblies 72, 94 to the triaxial test specimen 112.

The vertical loading assembly 28 further includes the vertical clamping assembly 38 that functions to vertically and rigidly clamp the triaxial test specimen 112 (not shown in FIG. 2) in place during operation of the triaxial test apparatus 10. The vertical clamping assembly 38 is pivotably connected to the loading bar 34 by a first latch 44. The first latch 44 mechanically engages the notch 46 by a first swivel pin 40, thereby enabling the vertical clamping assembly 38 to freely pivot and rotate in response to forces transferred to it by the vertical loading assembly 28. Forces imparted to the vertical loading assembly 28 are further transferred to vertical load transfer plate 42 and to vertical clamp 48. The vertical clamp 48 is connected to the vertical load transfer plate 42 by bolts, screws or other such mechanical fasteners, and the vertical clamp 48 and the load transfer plate 42 function together to transfer vertical and shear loads to, and vertically and rigidly clamp, the triaxial test specimen 112 in place during operation of the triaxial test apparatus 10.

FIG. 2 shows one vertical loading assembly 28 and one vertical clamping assembly 38 connected together; but the preferred embodiment of the present invention has at least two sets of such connected assemblies, each set axially disposed in relation to the other and rigidly clamping (vertically) opposing ends of triaxial test specimen 112. One vertical clamping assembly 38 is pivotably connected to the attachment bar 30 and the other is pivotably connected to the loading bar 34. As disclosed above, the vertical loading assembly 28 and vertical clamping assembly 38 may be made of any suitable structural material that may be manufactured into extruded shapes, plates and pins, and so forth by conventional machining, molding, forging and the like so as to provide vertical loading and vertical clamping parts that have high structural strength, high structural stiffness and minimal weight.

Referring to FIGS. 1 and 2 together, the vertical loading assembly 28 is connected at opposing ends to the top and bottom joint assemblies 72, 94 by conventional mechanical means so that forces imparted by the testing machine 126 to the top and bottom joint assemblies 72, 94 are proportionally transferred to the vertical loading assembly 28, and thence to the vertical clamping assembly 38. The vertical clamping assembly 28 is vertically and rigidly clamped to the triaxial test specimen 112. Thus, forces from the testing machine 126 are transferred by the vertical loading assembly 28 and by the vertical clamping assembly 38 as vertical compression, vertical tension and shear loads, and combinations thereof, to the triaxial test specimen 112.

Figure 3:
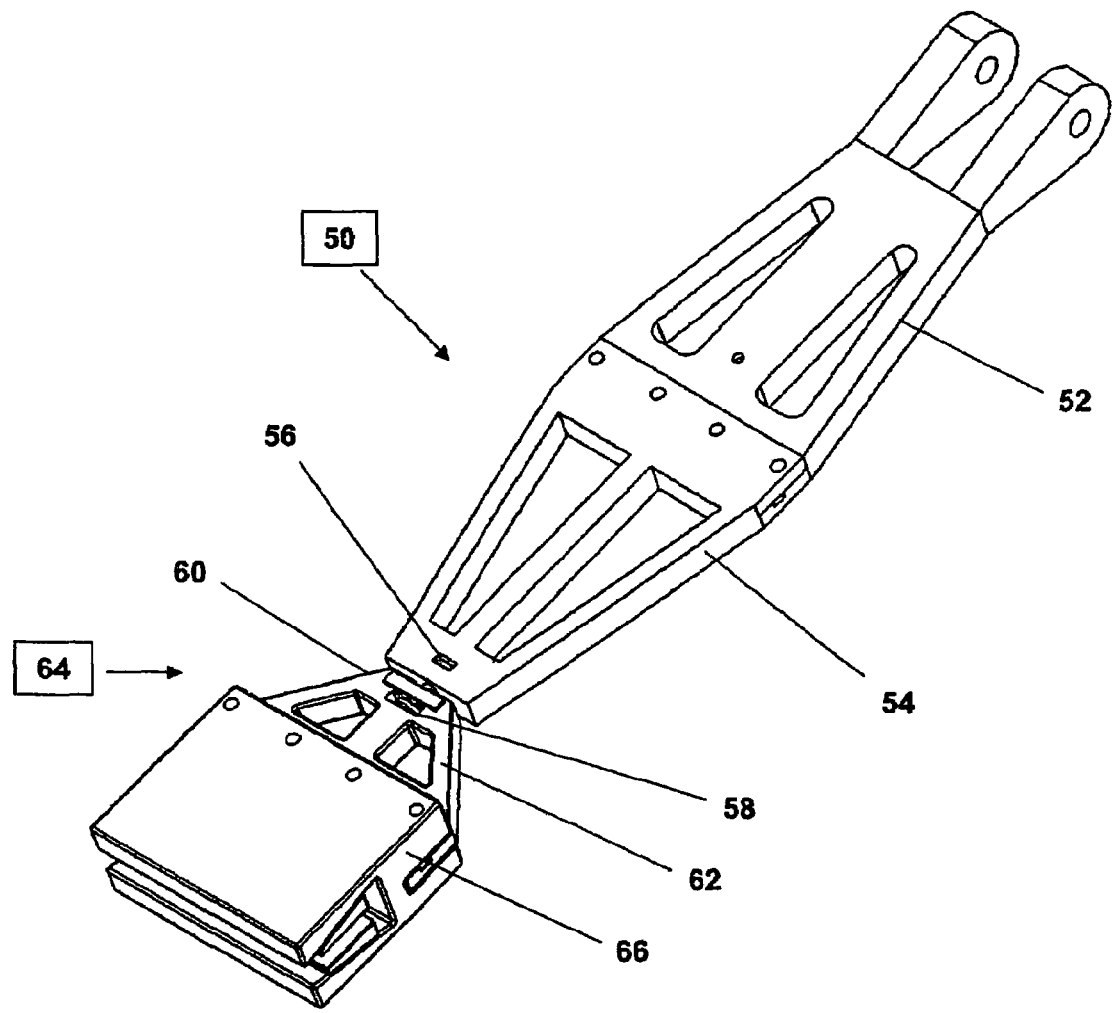
FIG. 3 shows a perspective view of a horizontal loading assembly in accordance with an embodiment of the apparatus of present invention.

FIG. 3 shows a perspective view of the horizontal loading assembly 50, and of the horizontal clamping assembly 64, in accordance with an embodiment of the present invention. The horizontal loading assembly 50 comprises horizontal load transfer plate 52 and extension loading plate 54 that are connected together by bolts, screws or other such mechanical fasteners. One end of the horizontal loading assembly 50 is configured to receive the bracket pin 18 and functions to pivotably connect each horizontal loading assembly 50 to a pair of the linkage 20–26, and thereby enables the horizontal loading assembly 50 to pivot in relation to the linkages 20–26 and in relation to the top and bottom joint assembles 72, 94. A second end of each horizontal loading assembly 50 is pivotably connected to the horizontal clamping assembly 64. The extension loading plate 54 is connected to clamp plate 62 by second latch 60. The second latch 60 mechanically engages the clamp plate 62 by second swivel pin 58 disposed within cavity 56; thereby enabling the horizontal clamping assembly 64 to freely pivot and rotate in response to force transferred to it by the horizontal loading assembly 50. Forces imparted to the clamp plate 62 are further transferred to horizontal clamp 66. The clamp plate 62 is connected to the horizontal clamp 66 by bolts, screws or other such mechanical fasteners, and the clamp plate and horizontal clamp function together to transfer horizontal and shear loads to, and to rigidly clamp in place, the triaxial test specimen 112 during operation of the triaxial test apparatus 10.

FIG. 3 shows one horizontal loading assembly 50 and one horizontal clamping assembly 64, but the preferred embodiment of the present invention has at least four of such combined assemblies, orthogonally disposed in relation to each other and clamping four ends of the triaxial test specimen 112. As discussed above each horizontal clamping assembly 64 is connected to a horizontal loading assembly 50, and each horizontal loading assembly 50 is connected is configured to receive the bracket pin 18. The bracket pin 18 functions to pivotably connect each horizontal loading assembly 50 to a pair of linkages 20–26, and thereby enables each horizontal loading assembly 50 to pivot in relation to the linkages 20–26 and in relation to the top and bottom joint assembles 72, 94. As disclosed above, the horizontal loading assembly 50 and the horizontal clamping assembly 64 may be made of any suitable structural material that may be manufactured into extruded shapes, plates and pins, and so forth by conventional machining, molding, forging and the like so as to provide horizontal loading and horizontal clamping parts that have high structural strength, high structural stiffness and minimal weight.

Referring to FIGS. 1 and 3 together, each horizontal loading assembly 50 is connected at one end (by a corresponding bracket pin 18) to a pair of linkages 20–26 so that forces imparted by the testing machine 126 to the top and bottom joint assemblies 72, 94 are proportionally transferred to the horizontal loading assembly 50, and then to the horizontal clamping assembly 64. The horizontal clamping assembly 64 is rigidly clamped to the triaxial test specimen 112. Thus, forces from the testing machine 126 are transferred as horizontal compression, horizontal tension and shear from the horizontal loading assembly 50 and the horizontal clamping assembly 64 as horizontal compression, horizontal tension and shear loads, and combinations thereof, to the triaxial test specimen 112.

Figure 4:
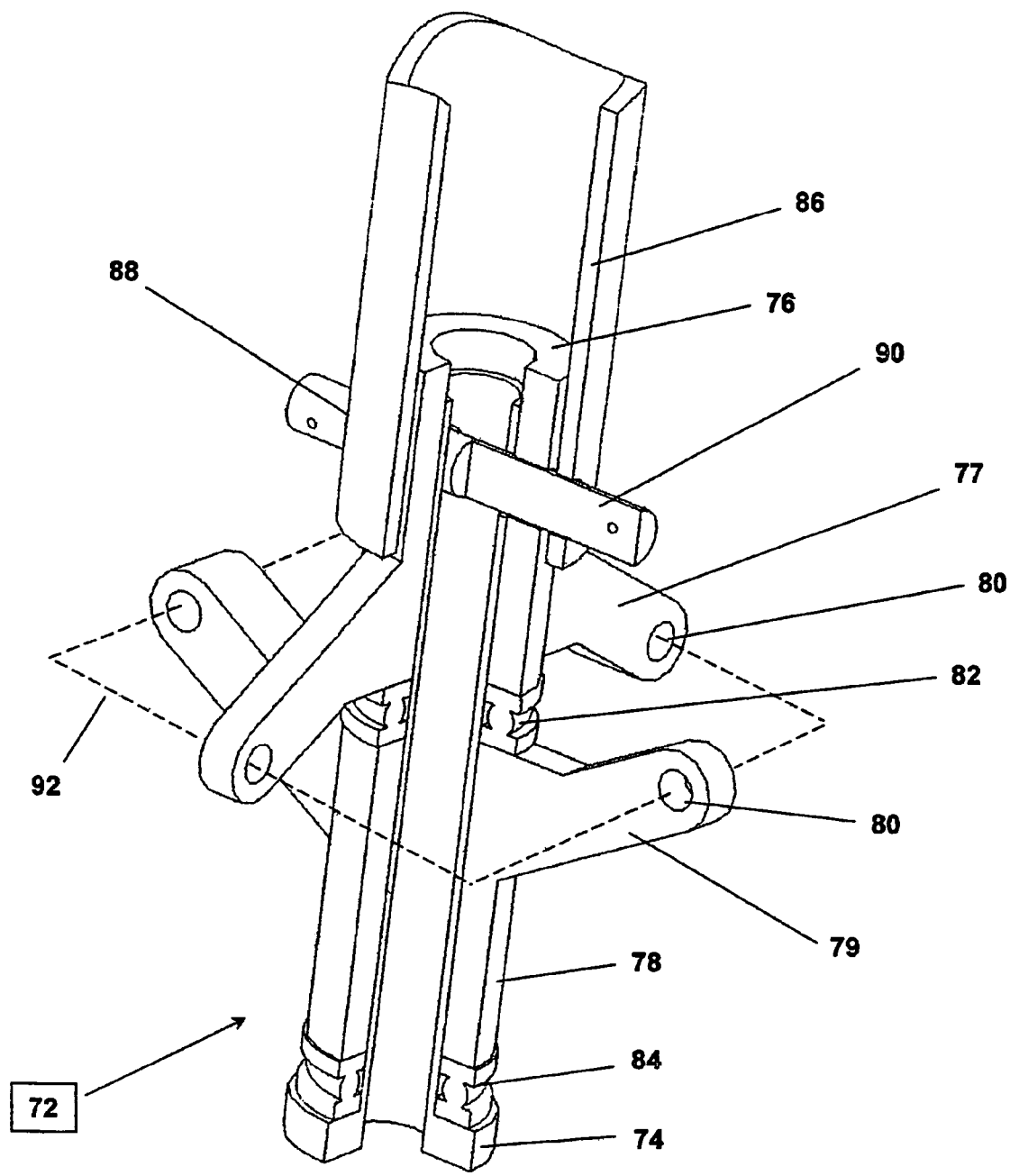
FIG. 4 shows a cross-sectional view of a joint assembly in accordance with an embodiment of the apparatus of the present invention.

FIG. 4 shows a cross-sectional view of a (top or bottom) joint assembly in accordance with an embodiment of the apparatus of the present invention. The structure of the top and bottom joint assemblies 72, 94 is the same, and FIG. 4 representatively illustrates the structure of the top joint assembly 72. The top joint assembly 72 comprises the first sleeve 76 and the second sleeve 78, the first thrust bearing 82, the second thrust bearing 84, top connecting rod 74 and the top pin 90. The first sleeve 76 includes apertures 80 at the distal end of downward extending arms 77 as pivoting connecting points for the horizontal force members 12. Similarly the second sleeve 78 includes apertures 80 at the distal end of upward extending arms 79 as pivoting connecting points for the horizontal force members 12. During loading for a test, the position of the apertures 80 of the top joint assembly 72 are on a horizontal plane 92, in which the horizontal plane is allowed by the first sleeve 76 having the downward extending arms 77 and the second sleeve 78 having the upward extending arms 79.

The top connecting rod 74 is axially disposed through the longitudinal axes of the first and second sleeves 76, 78 and functions to hold the sleeves in place adjacent to each along their common longitudinal axis. The first thrust bearing 82 is disposed between the first and second sleeves 76, 78, and the second thrust bearing 84 is disposed adjacent to one end of the second sleeve 84. Top pinhole 88 is formed through the top crosshead 86, the top connecting rod 74 and the top first sleeve 76 and is configured to receive the top pin 90. The top pin 90 is inserted through the top pinhole 88, thereby rigidly connecting the top crosshead 86 to the top joint assembly 72. The top crosshead 86 functions to receive forces from the testing machine 126 (not shown in FIG. 4) and transfer the forces to the top joint assembly 72.

In further reference to FIG. 4, the first and second sleeves 76, 78 are able to rotate freely in relation to each other about the longitudinal axis defined by the top connecting rod 74. First and second sleeves are also able to move along the longitudinal axis of the top connecting rod 74, but are restrained by the pin 90 from moving longitudinally in the direction of the top crosshead 86. Thus, the pin 90 restrains the longitudinal motion of the first and second sleeves 76, 78, yet allows rotation of one sleeve with respect to the other.

Referring again to FIG. 1, the bottom joint assembly 94 is similarly constructed to the top joint assembly 72, with the bottom joint assembly 94 comprising the third sleeve 98, the fourth sleeve 100, the third thrust bearing 102, the fourth thrust bearing 104 and the bottom pin 110. An additional pair of extending arms may be positioned on the third sleeve 98, similar to the positioning of the downward extending arms 77 on the first sleeve 76. Similarly, an additional pair of upward extending arms may be positioned on the fourth sleeve 100. Similarly to the top connecting rod 74 disclosed above, bottom connecting rod 96 is axially disposed through the third and fourth sleeves 98, 100 along a common longitudinal axis. The third thrust bearing 102 is disposed between the third and fourth sleeves 98, 100, and the fourth thrust bearing 104 is disposed adjacent to one end of the fourth sleeve 100. The bottom pin 110 is inserted through bottom pinhole 108, thereby rigidly connecting bottom the crosshead 106 to the bottom joint assembly 94. The bottom crosshead 106 functions to receive forces from the testing machine 126 and transfer the forces to the bottom joint assembly 94.

FIGS. 1 and 4 together show that the top and bottom joint assemblies 72, 94 are thusly constructed to enable the first and second sleeves 76, 78 and the third and fourth sleeves 98, 100 to rotate freely about and along the longitudinal axis defined, respectively, by the top connecting rod 74 and the bottom connecting rod 96. The longitudinal motion of each joint assembly, however, is restricted in the direction of the top and bottom crossheads 86, 106 by the action of the top pin 90 and the bottom pin 110 inserted through the respective top and bottom pinhole. In this manner, longitudinal forces (represented by arrow A and arrow B of FIG. 1) and rotational force (represented by arrow C of FIG. 1) imparted to the top or bottom crosshead 86, 106 by the testing machines 126 are directly transferred by the top or bottom pins 90 or 110 and to the first, second, third and fourth sleeves 76, 78, 98, 100. The according rotational and linear movement of the top and joint assemblies 72, 94 acts to impart compressive, tensile and shear loads to the test specimen 112, as further disclosed below.

Figure 5:
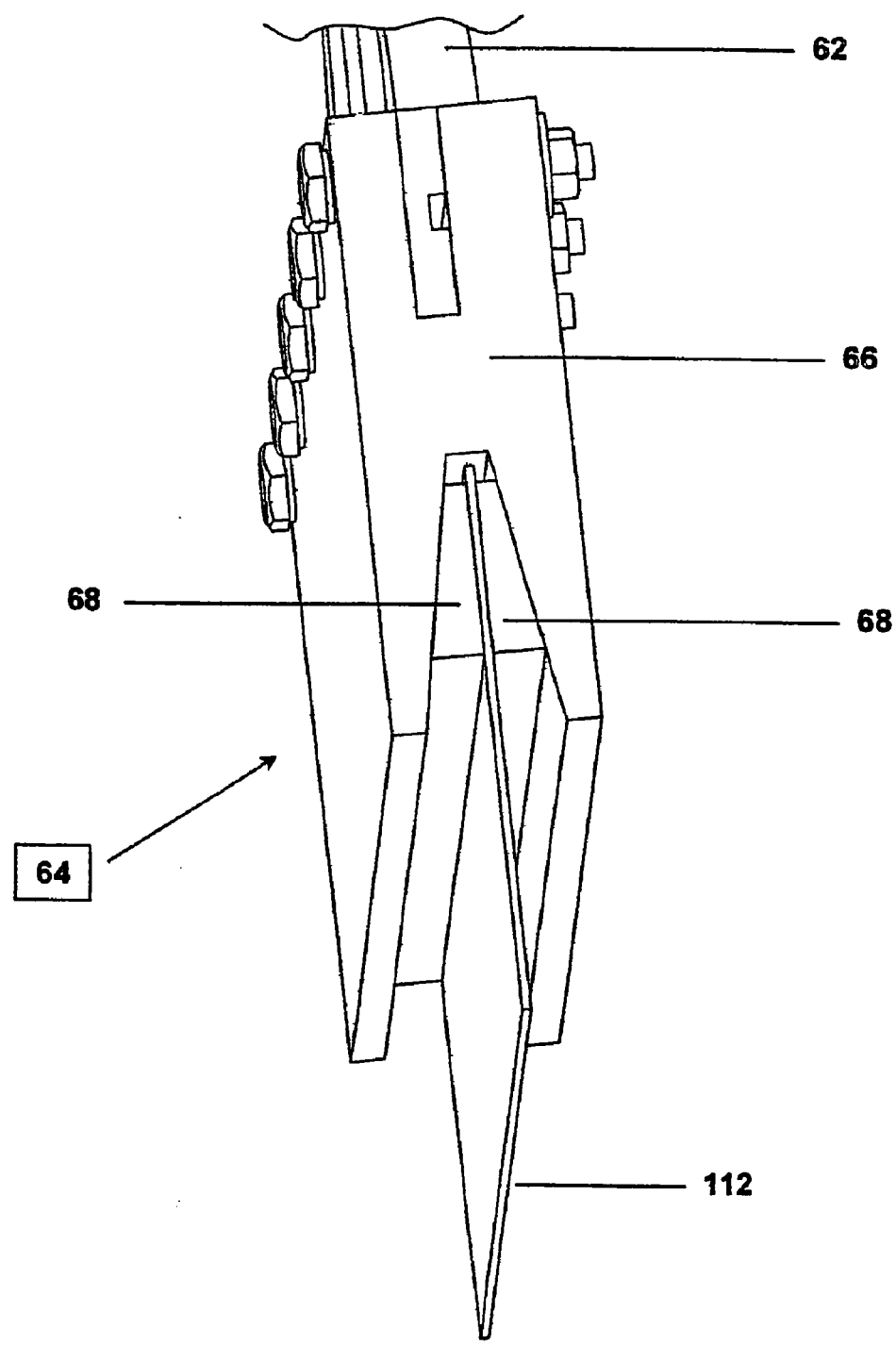
FIG. 5 shows a perspective view of a clamping assembly in accordance with an embodiment of the apparatus of the present invention.

FIG. 5 shows a perspective view of a clamping assembly in accordance with an embodiment of the apparatus of the present invention. The clamping assembly of FIG. 5 may interchangeably be used as part of the vertical clamping assembly 38 or as part of the horizontal clamping assembly 64, and the following disclosure applies to either the horizontal or the vertical clamping assemblies. Here, FIG. 5 representatively discloses that the horizontal clamping assembly 64 includes the clamp plate 62 connected to the clamp 66 by several nuts and bolts. Other similar mechanical fasteners or fastening methods (welding, brazing and so forth) may be used, provided that such fasteners or methods function to rigidly connect the clamp plate 62 to the clamp 66.

The clamp 66 further includes wedge 68 disposed within and connected to a distal end of the clamp. The wedges 66 function to frictionally hold the triaxial test specimen 112 in place for compressive loading of the test specimen during operation of the triaxial testing apparatus 10. For tensile loading of the triaxial specimen 112 and preferable if the specimen is a planar solid, only one of the two wedges shown in FIG. 5 is connected within the distal end of the clamp 66. For compressive loading of the triaxial test specimen 112, FIG. 5 (two) wedges are disposed within and connected to a distal end of the clamp 66. The horizontal clamping assembly 64 thus functions to rigidly clamp test specimens, preferably planar solid specimens, in the triaxial test apparatus 10 for tensile, compressive and shear loading during material properties testing.

Figure 6:
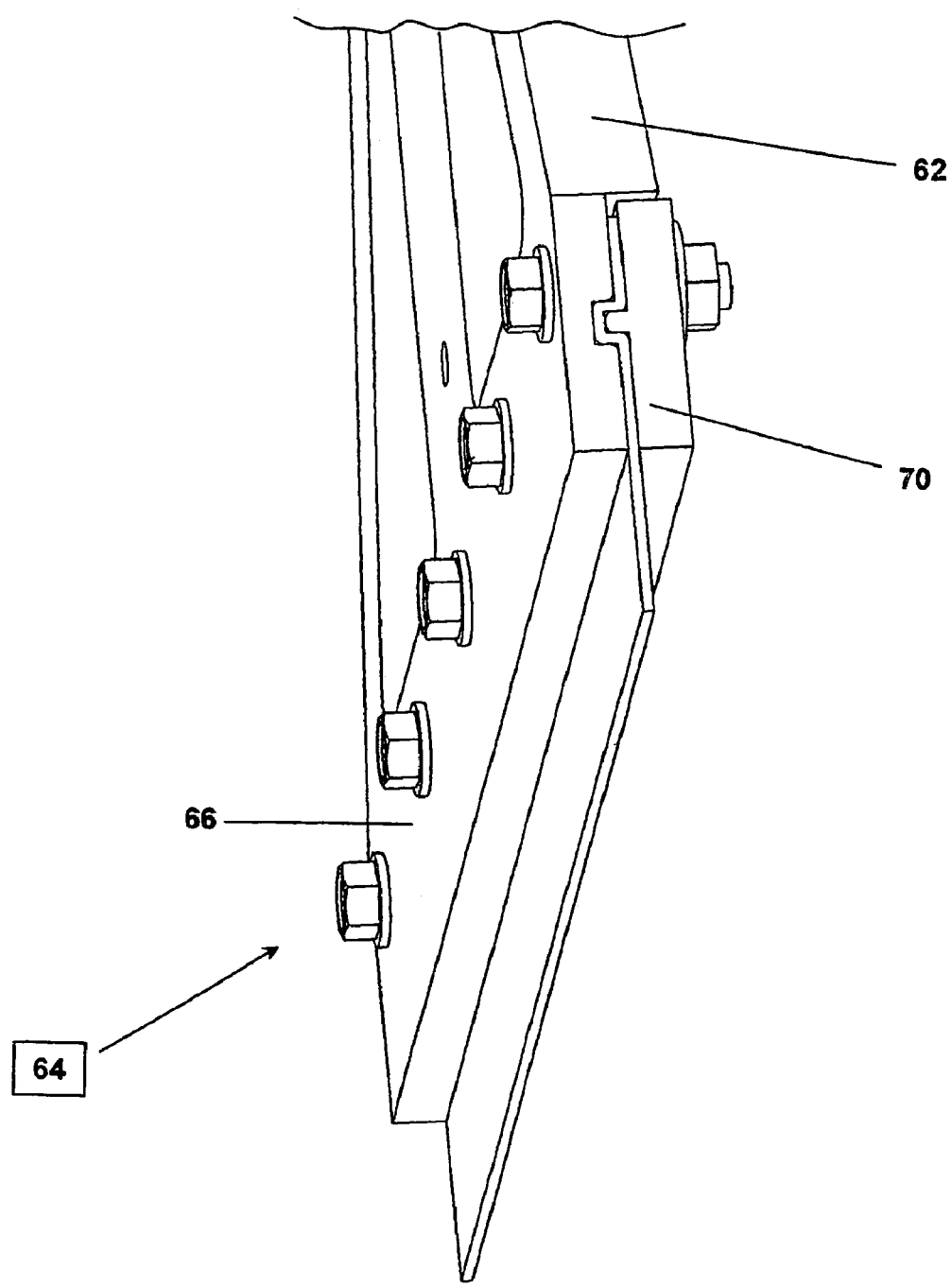
FIG. 6 shows a perspective view of an alternative clamping assembly in accordance with an embodiment of the apparatus of the present invention.

FIG. 6 shows a perspective view of an alternative clamping assembly in accordance with an embodiment of the apparatus of the present invention. The clamping assembly of FIG. 6 may interchangeably be used as part of the vertical clamping assembly 38 or as part of the horizontal clamping assembly 64, and the following disclosure applies to both clamping assemblies. Here, FIG. 6 representatively discloses that for loading of fabric or other bendable material test specimens, the horizontal clamping assembly 64 uses tongue and groove clamp 70 to secure the specimen within opposing plates of the clamp 66. Similarly to the clamping assembly disclosed in FIG. 5 above, FIG. 6 shows that the clamp plate 62 is connected to the clamp 66 by several nuts and bolts. The nuts and bolts also function to frictionally clamp the specimen within the disclosed tongue and groove structure. Other similar mechanical fasteners or fastening methods (welding, brazing and so forth) may be used, provided that such fasteners or methods function to rigidly connect the clamp plate 62 to the clamp 66. The horizontal clamping assembly 64 thus functions to rigidly clamp test specimens, preferably fabric or other bendable material specimens, in the triaxial test apparatus 10 for tensile, compressive and shear loading during material properties testing.

Figure 7:
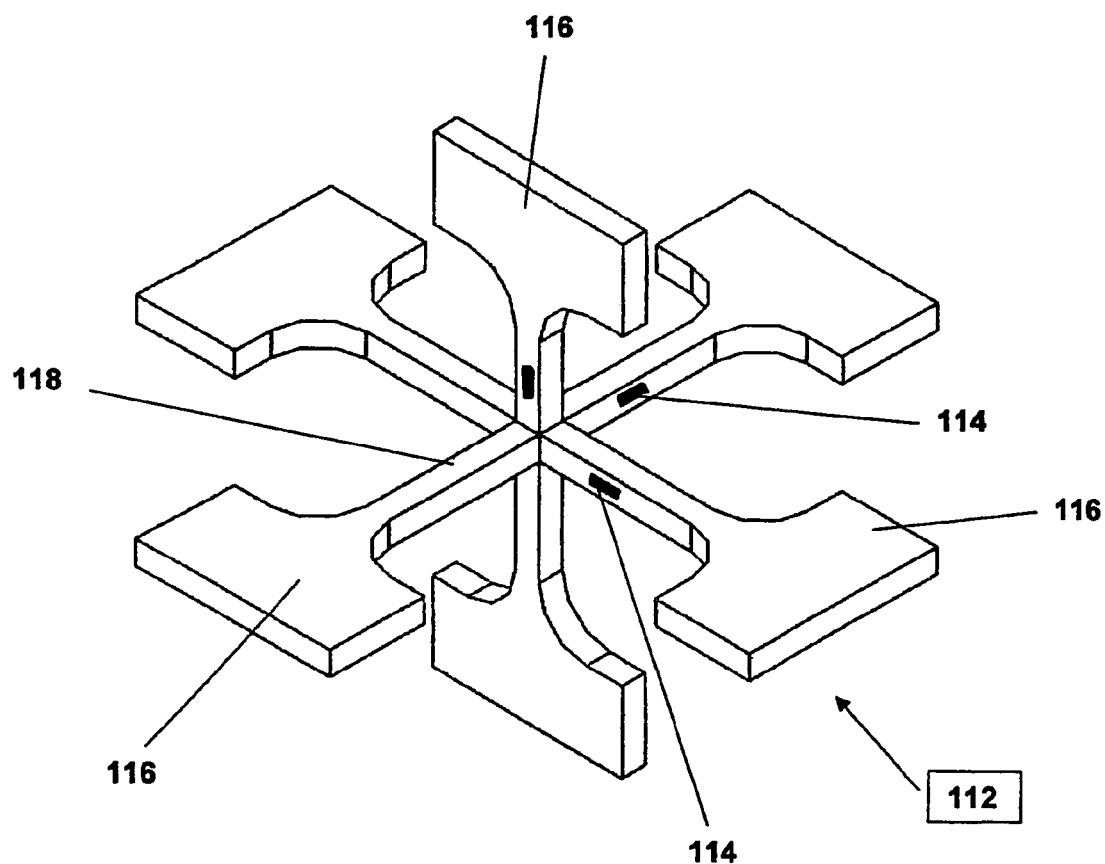
FIG. 7 shows an isometric view of a test specimen in accordance with an embodiment of the apparatus of the present invention.

FIG. 7 shows an isometric view of the triaxial test specimen 112 in accordance with an embodiment of the apparatus of the present invention. The triaxial test specimen 112 comprises at least three opposing pairs of ends 116 connected together by corresponding bases 118. The ends 116 are shaped for to optimize clamping by either of the horizontal and vertical clamping assemblies 64, 38 disclosed above and illustrated by FIGS. 5 and 6. FIG. 7 shows that the bases 118 are shaped to uniformly transfer axial vertical and horizontal compressive and tensile loads throughout the triaxial test specimen 112 during operation of the triaxial testing apparatus 10.

FIG. 7 also shows the load measurement devices 114 that may comprise any conventional strain gauge suitable for measuring and/or recording the axial displacement of the specimen, and thereby the axial loads, where the triaxial test specimen 112 is made of solid materials. For fabric specimen (not illustrated), a conventional displacement wire transducer, or a conventional Linear Variable Displacement Transducer Device (LVDT) may be used for the load measurement devices 114 to thereby measure axial and shear loads imparted to the test specimen. The triaxial test specimen 112 thus functions to provide a test specimen that has ends shaped to optimize clamping, bases optimized to uniformly transfer axial loads throughout the specimen and to provide load measurement devices for measuring and/or recording axial and shear loads imparted to the specimen during operation of the triaxial testing apparatus 10.

Figure 8:
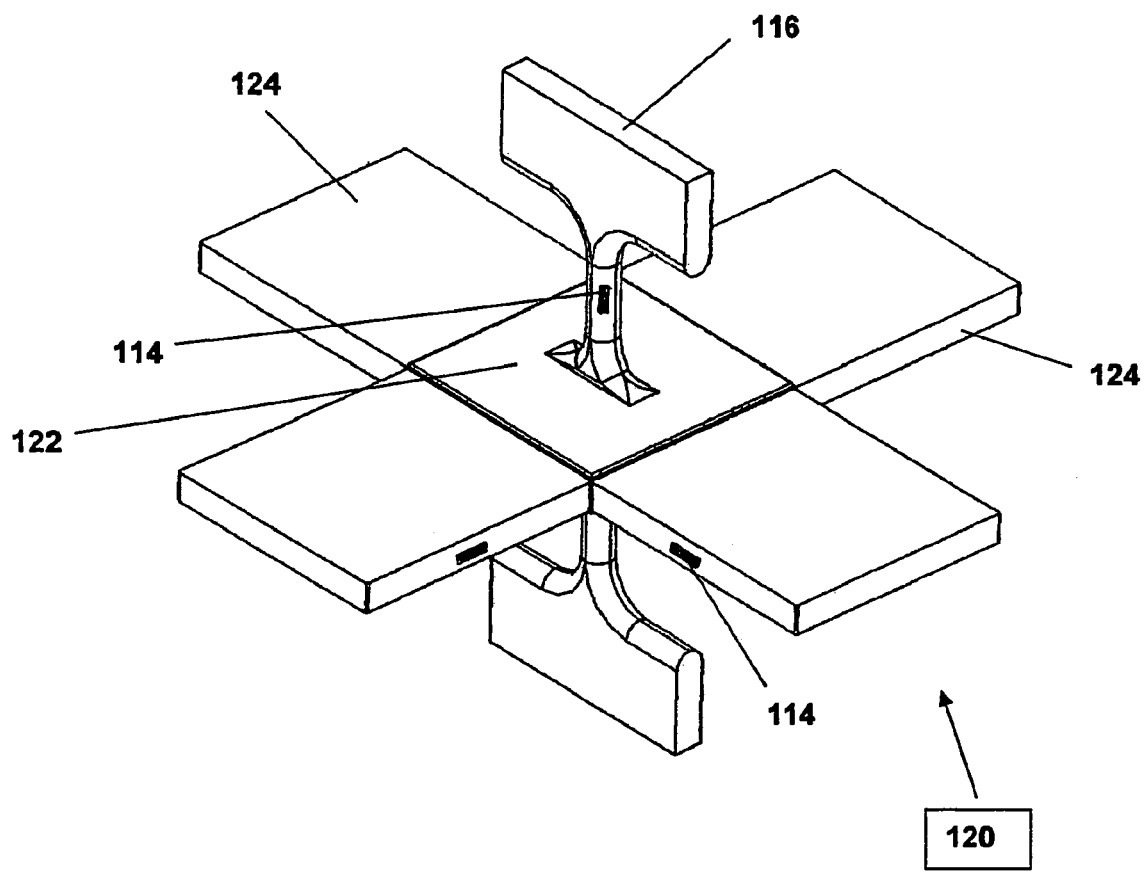
FIG. 8 shows an isometric view of an alternative test specimen in accordance with an embodiment of the apparatus of the present invention.

FIG. 8 shows and isometric view of an alternative test specimen in accordance with an embodiment of the apparatus of the present invention. Plane-triaxial test specimen 120 includes planar horizontal ends 124 that are connected together by plates 122 on the top and the bottom of the intersection area of the planar horizontal sides. Preferably, the plates 122 are constructed of rigid materials that will hold the ends 124 in place during vertical loading of the test specimen. The planar horizontal ends 124 and plates 122 function together to horizontally stabilize composite specimens within the horizontal clamping assembly during operation of the triaxial testing apparatus 10 so that a uniform axial vertical tensile or compressive load is imparted at the center of the plane-triaxial test specimen 120 when the ends 116 are subjected to vertical loading imparted by the vertical clamping assembly 38. The load measurement devices 114 are disposed on the ends 116 and the planar horizontal sides to measure the axial displacement, and thereby the axial stress where the triaxial test specimen 120 is made of composite materials. The plane-triaxial test specimen 120 thus functions to provide a spatially stabilized apparatus for composite specimen that has ends planar horizontal ends for horizontally stabilizing the specimen, ends for vertical clamping and load measurement devices for measuring loads imparted to the specimen.

Figure 9:
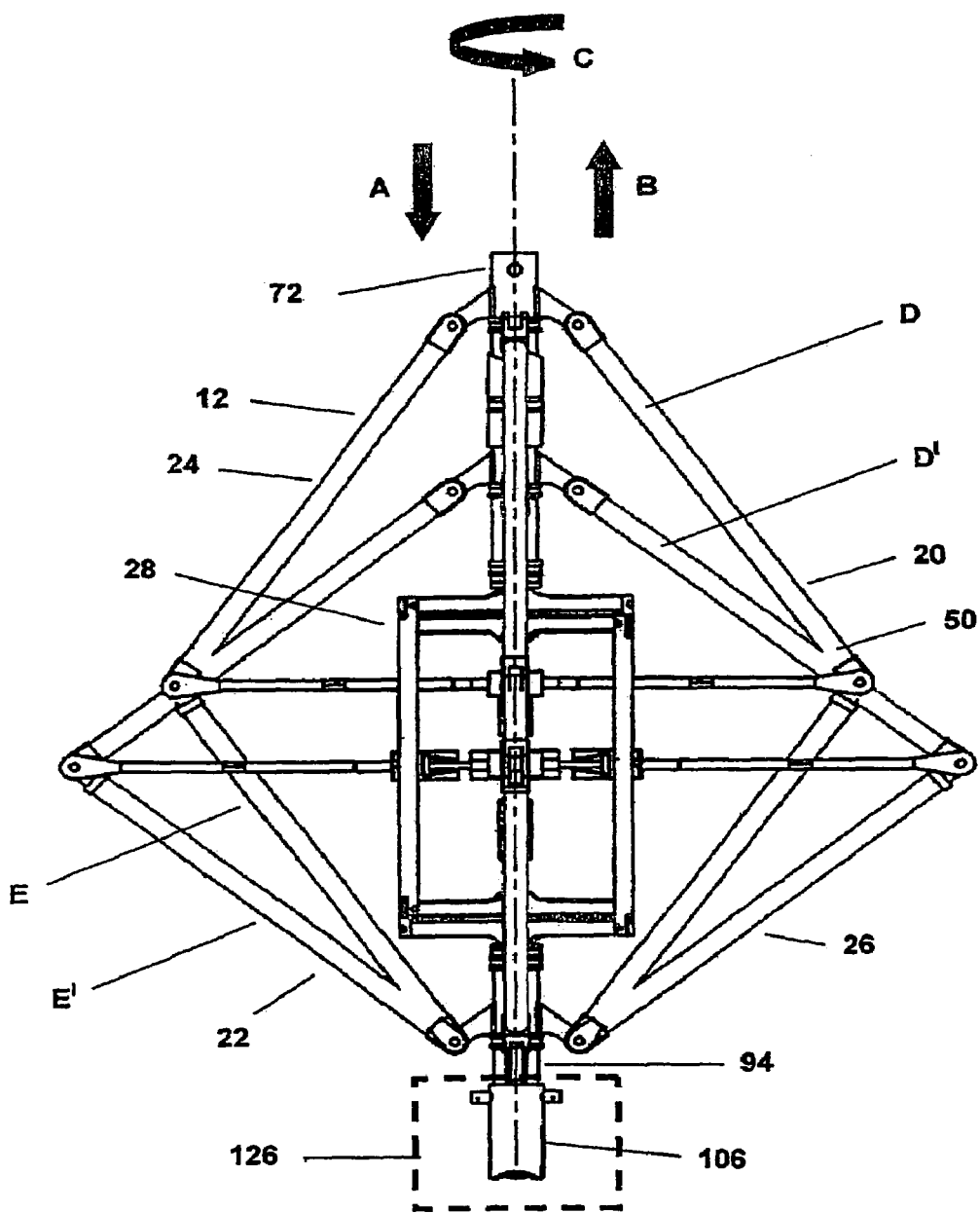
FIG. 9 shows a side schematic view of the movement of the triaxial testing apparatus during operation in accordance with an embodiment of the apparatus of the present invention.

FIG. 9 shows a side schematic view of the movement of triaxial testing apparatus during operation in accordance with an embodiment of the apparatus of the present invention. As discussed and illustrated by FIG. 1, the testing machine 126 may be connected to the bottom joint assembly 94 for imparting forces to the triaxial testing apparatus 10.

FIGS. 1 and 9 show the testing machine 126 connected to the bottom joint assembly 94, but those skilled in the art understand that the testing machine may be connected to either the bottom joint assembly 94 or to the top joint assembly 72. Since the top and bottom joint assemblies 72, 94 are connected to each other by the horizontal force members 12; the horizontal force members transfer forces imparted to one of the joint assemblies to the other joint assembly. Accordingly, force imparted by the testing machine 126 to either of the top and bottom joint assemblies 72, 94 is transferred to the horizontal loading assembly 72 and to the vertical loading assembly 94. The loading assemblies, in turn, directly transfer the forces to the triaxial test specimen 112. Thus, the triaxial testing apparatus 10 functions to transfer longitudinal and rotational forces from the testing machine 126 as compression, tensile and shear loads to the triaxial test specimen 112.

Referring to FIGS. 1 and 9 together, force arrow A represents downward longitudinal force imparted by the testing machine 126 to the top joint assembly 72 (or to bottom joint assembly 94). Force arrow B represents upward longitudinal force imparted by the testing machine 126 to the top joint assembly 72 (or to the bottom joint assembly 94). Force arrow C represents rotational force imparted by the testing machine 126 to the top joint assembly 72 (or to the bottom joint assembly 94). Force arrow A, representing longitudinal force imparted to the triaxial testing apparatus 10 by the testing machine 126, causes the top joint assembly 72 to move downward. The downward motion of the top joint assembly 72 causes the linkages 20 and 24, to correspondingly move downwards and outwards from the longitudinal axis, as illustrated by D and D' of FIG. 9. The linkages 22 and 26 are connected to the linkages 20 and 24 by the bracket links 16. Thus, the downward motion of top joint assembly 72 also causes the linkages 22 and 26 to move downwards and outwards from the longitudinal axis, as illustrated by E and E' of FIG. 9. The linkages 20, 22, 24, and 26 thereby increase in distance from each other in relation to the assembly configuration of FIGS. 1 and 9. The increase in distance between the linkages 20–26 causes the horizontal loading assembly 50 to impart the tensile load and vertical loading assembly 38 to impart tensile load to the triaxial test specimen 112. Thus, the triaxial testing apparatus 10 functions to transfer force imparted to it by the testing machine 126 as a first axis (horizontal tension) and a third axis (vertical tensile) load to the triaxial test specimen 112.

In further reference to FIG. 9, force arrow B represents upward longitudinal force imparted by the testing machine 126 to the top joint assembly 72 (or to the bottom joint assembly 94). Force arrow B, representing longitudinal force imparted to the triaxial testing apparatus 10 by the testing machine 126, causes the top joint assembly 72 to move upward. The upward motion of the top joint assembly 72 causes the linkages 20 and 24, to correspondingly move upwards and in towards the longitudinal axis, as illustrated by D' and D of FIG. 9. The linkages 22 and 26 are connected to the linkages 20 and 24 by the bracket links 16. Thus, the upward motion of the top joint assembly 72 also causes the linkages 22 and 26 to move upwards and in towards the longitudinal axis, as illustrated by E' and E of FIG. 9. The linkages 20, 22, 24, and 26 thereby decrease in distance from each other in relation to the assembly configuration of FIGS. 1 and 9. The decrease in distance between the linkages 20–26 causes the horizontal loading assembly 50 to impart the compressive load and vertical loading assembly 38 to impart compressive load to the triaxial test specimen 112. Thus, the triaxial testing apparatus 10 functions to transfer force imparted to it by the testing machine 126 as a second axis (horizontal compression) and a third axis (vertical compression) load to the triaxial test specimen 112.

Force arrow C of FIG. 9 represents rotational force imparted by the testing machine 126 to the top joint assembly 72 (or to the bottom joint assembly 94). Force arrow C, representing rotational force imparted to the triaxial testing apparatus 10 by the testing machine 126 causes the top joint assembly 72 to rotate around the longitudinal axis. The rotational movement of the top joint assembly 72 causes the linkage 20 and 24 to also rotate about the longitudinal axis. The linkages 22 and 26 are connected to the linkages 20 and 24 by the bracket links 16. Thus, the rotational movement of the top joint assembly 72 also causes the linkages 22 and 26 to rotate about the longitudinal axis. The rotational movement of the linkages 20–26 causes the horizontal loading assembly 50 and the vertical loading assembly 38 to impart shear load to the triaxial test specimen 112. Thus, the triaxial testing apparatus 10 functions to transfer force imparted to it by the testing machine 12 as shear loads to the triaxial test specimen 112.

How to Use an Embodiment of the Invention

Referring collectively to FIGS. 1–9, an embodiment of the invention is used in the following manner. First, the triaxial testing machine 126 is rigidly connected to either the top or bottom crosshead 86, 106 by the top pin 90 or by the bottom pin 110. Second, the ends 116 of the triaxial test specimen 112 are rigidly connected to the clamp plates 62 of the horizontal clamping assembly 50 and to the vertical clamps 48 of the vertical clamping assembly 38. For tensile and compressive loading of the solid test specimens 112, the wedge clamping assembly of FIG. 5 is used to secure the test specimen 112 to the horizontal clamping assembly 50 and to the vertical clamping assembly 38. The wedges 68 are used to frictionally hold the triaxial test specimen 112 in place during compressive loading of the test specimen during operation of the triaxial testing apparatus 10. For tensile loading of the solid triaxial specimens 112 only one of the two wedges shown in FIG. 5 is connected within the distal end of the clamp 66. For testing composite specimens, the plane-triaxial test specimen 120 of FIG. 8 is used, wherein the planar horizontal sides 124 of the test specimen are connected together by the plates 122 on the top and the bottom of the intersection area of the planar horizontal sides. For testing fabric specimens the tongue and groove clamping assembly of FIG. 6 is used to secure the test specimen to the horizontal clamping assembly 50 and to the vertical clamping assembly 38.

Third, once the triaxial test specimen 112 is rigidly connected to the horizontal and vertical clamping assemblies 50, 38, the testing machine 126 is operated to impart the desired longitudinal and rotational forces to the top or bottom crossheads 86, 106. As disclosed above, the forces imparted by the testing machine 126 to the crossheads 86, 106 are directly transferred to the top and bottom joint assemblies 72, 94, to the linkages 20, 22, 24, 26, to the horizontal and vertical loading assemblies 38, 50, and thereby to the triaxial test specimen 112.

As further disclosed above, the longitudinal downward, upward or rotational movement of the top and bottom crossheads 86, 106 causes corresponding upward, downward or rotational movement of the linkages 20–26, and also caused the linkages to move outward from or inwards to the longitudinal axis. The longitudinal movement of the linkages 20–26 causes horizontal compression or horizontal tension loads to be imparted to the triaxial test specimen 112 by the horizontal loading assembly 50. The rotational movement of the linkages 20–26 causes shear loads to be imparted to the triaxial test specimen 112 by the horizontal loading assembly 50. Similarly, longitudinal movement of the top or bottom joint assemblies 72, 94 causes vertical compression or vertical tension loads to be imparted to the triaxial test specimen 112 by the vertical loading assembly 28. Rotational movement of the top or bottom joint assemblies 72, 94 causes shear loads to be imparted to the triaxial test specimen 112 by the vertical loading assembly 28.

Those skilled in the art will realize that either of the top or bottom crossheads 86, 106 may be rigidly fixed in relation to the frame of the testing machine 126, while the other crosshead is free to rotate in response to rotational forces from the testing machine. Thus, for example, the top crosshead 86 may be connected (by the pin 90) to the testing machine 126, and the bottom crosshead 106 may be rigidly fixed in relation to the frame of the testing machine. Accordingly, rotation of the top crosshead 86 will rotate the first sleeve 76 of the top joint assembly 72, and thereby rotate the linkages 20 and 24. The linkages 22 and 26 will remain stationary, as the linkages are attached to the bottom crosshead 106, which is rigidly connected to the frame of the testing machine 126. Thus, the horizontal loading assemblies 50 will rotate with respect to one another and apply a pure shear load to the triaxial test specimen 112.

Fourth, the triaxial testing specimen 112 may include the conventional load measurement devices 114 that may further include conventional strain gauges, to measure and/or record the axial displacement, and strain, and thereby the axial stress where the triaxial test specimen 112 is made of solid materials. For a fabric specimen (not illustrated), a conventional displacement wire transducer, or a conventional Linear Variable Displacement Transducer Device (LVDT) may be used for the load measurement devices 114 to thereby measure axial force imparted to the triaxial test specimen 112.

Therefore, the triaxial testing apparatus 10 may be used to transfer loads from the testing machine 126 to the triaxial test specimen 112, or to the plane-triaxial test specimen 120, or to a fabric specimen (not illustrated). The triaxial testing apparatus 10 is configured to simultaneously impart compression, tension, and shear loads to the test specimen in at least three axes, including horizontal compression, horizontal tension, vertical compression, vertical tension, horizontal shear, and vertical shear loads and combinations thereof. Those skilled in the art will realize that the triaxial testing apparatus 10 may also be used to impart uniaxial tension, uniaxial compression, biaxial tension, biaxial compression, triaxial tension, triaxial compression, uniaxial tension with in-plane shear, uniaxial compression with in-plane shear, biaxial tension with in-plane shear, biaxial compression with in-plane shear, triaxial compression with in-plane shear, unequal triaxial tension with in-plane shear, and unequal triaxial compression with in plane shear loads to the test specimen.

Advantages of an Embodiment of the Invention

An advantage of an embodiment of the present invention is that it provides a triaxial testing apparatus that is capable of applying a combined in-plane shear and multi-axial loads to a test specimen. As disclosed above, during operation of the present invention, forces imparted by the testing machine 126 to the top or bottom crossheads 86, 106 are directly transferred to the top and bottom joint assemblies 72, 94, to the linkages 20, 22, 24, 26, to the horizontal and vertical loading assemblies 38, 50, and thereby to the triaxial test specimen 112. As further disclosed above, the longitudinal downward, upward or rotational movement of the top and bottom crossheads 86, 106 causes corresponding upward, downward or rotational movement of the linkages 20–26, and also caused the linkages to move outward from or inwards to the longitudinal axis. Longitudinal movement of the linkages 20–26 causes horizontal compression or horizontal tension loads to be imparted to the triaxial test specimen 112 by the horizontal loading assembly 50. Rotational movement of the linkages 20–26 causes shear loads to be imparted to the triaxial test specimen 112 by the horizontal loading assembly 50. Longitudinal movement of the top or bottom joint assemblies 72, 94 causes vertical compression or vertical tension loads to be imparted to the triaxial test specimen 112 by the vertical loading assembly 28. Rotational movement of the top or bottom joint assemblies 72, 94 causes shear loads to be imparted to the triaxial test specimen 112 by the vertical loading assembly 28. Thus, the present invention provides a triaxial testing apparatus capable of applying combined shear and multi-axial loads to a test specimen.

Another advantage of an embodiment of the present invention is that it provides a single triaxial testing apparatus that is compact, cost-effective and easy to assemble and disassemble. In contrast to the prior art disclosed in the above (e.g., Lynch, Holt), the triaxial testing apparatus 10 consists of a single apparatus that includes integrated components capable of imparting in-plane and multi-axial loads to the test specimen 112. Moreover, the triaxial testing apparatus 10 is relatively compact in size and may be configured to conform to the dimensions of the testing machine 126 and the testing environment. As disclosed above, triaxial testing apparatus is constructed so that a user may conveniently assemble and disassemble and maintain it without the need for special tools or training. For instance, the bracket links 14, 16, the bracket pins 18, the attachment bar pin 36, the top and bottom pins 90, 100 and the fastening means for the horizontal clamp 66 and the tongue and groove clamp 70 are preferably chosen to facilitate convenient assembly, disassembly and repair of the triaxial testing apparatus 10.

A further advantage of an embodiment of the present invention is to provide test specimens that are configured to accurately and conveniently test the material properties testing of solid and composite specimens by a triaxial testing apparatus. For instance, as disclosed above, the triaxial test specimen 112 comprises at least three opposing pairs of the ends 116 connected together by corresponding bases 118. The ends 116 are shaped for optimal clamping by either of the clamping assemblies 38 or 64. The bases 118 are shaped to uniformly transfer axial vertical and horizontal compressive and tensile loads throughout the triaxial test specimen 112 during operation of the triaxial testing apparatus 10. The triaxial test specimen 112 also includes the load measurement devices 114 that may include conventional strain gauges, to measure the axial displacement, and strain and thereby the axial stress where the triaxial test specimen 112 is made of solid materials. The triaxial test specimen 112 thus functions to provide a test specimen that has ends conveniently adapted for clamping, bases optimized to accurately transfer axial loads thought the specimen and to provide load measurement devices for accurately and conveniently measuring loads imparted to the specimen.

CONCLUSION

There accordingly has been disclosed the triaxial testing apparatus 10 that comprises the plurality of horizontal force members 12 and the vertical loading assembly 28 connected together to the top joint assembly 72 and the bottom joint assembly 94. The horizontal force members 12 are further connected to the horizontal loading assembly 50 and the horizontal clamping assembly 64, and the vertical loading assembly 28 is similarly connected to the vertical clamping assembly 38. The horizontal clamping assembly 64 and the vertical clamping assembly 38 function together to clamp the triaxial test specimen 112 rigidly in place for material properties testing by the triaxial testing apparatus 10. The top joint assembly 72 includes the first and second sleeves 76, 78, and the bottom joint assembly 94 includes the third and fourth sleeves 98, 100, and each of the sleeves are configured to rotate independently of each other about and along a longitudinal axis in proportionate response to force imparted to the top crosshead 86 or to the bottom crosshead 106 by the testing machine 126. The longitudinal and rotational movements of the sleeves 76, 78, 98, 100 of the top and bottom joint assemblies 72, 94 are transferred by the horizontal force members 12 to the horizontal loading assembly 50, and by the vertical loading assembly 28 to the loading bar 34. The horizontal loading assembly 50 and the loading bar 34 further impart the longitudinal and rotational axial movement as horizontal compression, horizontal tension, vertical compression, vertical tension and shear loads, and combinations thereof, to the triaxial test specimen 112. The triaxial test specimen 112 includes the load measurement devices 114 for measuring and/or recording the compression, tensile and shear loads imparted by the triaxial testing apparatus 10 to the test specimen during material properties testing.

The reader's attention is directed to all papers and documents which are filed concurrently with this disclosure and which are open to public inspection with this specification, and the contents of all such papers and documents are incorporated herein by reference. All the features disclosed in this disclosure (including the accompanying claims, abstract and drawings) may be replaced by alternative features serving the same, equivalent or similar purpose unless expressly stated otherwise. Thus, unless expressly stated otherwise, each feature disclosed is but an example of a generic species of equivalent or similar features. Moreover, any element in a claim that does not explicitly state "means for" performing a specific function or "step for" performing a specific function is not be interpreted as a "means" or "step for" clause as specified by 35 U.S.C. 112 ¶ 6. In particular, any use of "step of" in the claims is not intended to invoke the provision of 35 U.S.C. 112 ¶.

What is claimed is:

1. A triaxial testing system of material properties, said system comprising:
   a test specimen with the material properties to be tested; and
   an apparatus wherein said apparatus comprises:
   a top and a bottom joint assembly, each of said assemblies having sleeves capable of rotational movement about and linear movement along a longitudinal axis;
   a plurality of horizontal force members having first and second ends, each of said horizontal force members connected at the first end to one of said joint assemblies for receiving the rotational and linear movement of said top and bottom joint assemblies;
   a plurality of horizontal loading assemblies, each of said horizontal loading assemblies connected to the second end of at least one of said horizontal force members for receiving the rotational and linear movement of said horizontal force members;
   a plurality of horizontal clamping assemblies, each of said horizontal clamping assemblies connected to said horizontal loading assemblies at an end opposite of said horizontal loading assemblies connected to said horizontal force members, for horizontally clamping said test specimen and for receiving the rotational and linear movement of said horizontal loading assemblies and transferring the movement as multi-axial and shear loading to said test specimen;
   a plurality of vertical force members connected to a sleeve of each of said top and bottom joint assemblies for receiving the rotational and linear movement of said top and bottom joint assemblies;
   a plurality of vertical loading assemblies connected to said vertical force members for receiving the rotational and linear movement of said vertical force members and;
   a plurality of vertical clamping assemblies, each of said vertical clamping assemblies connected to one of said vertical loading assemblies at an end opposite of said vertical loading assemblies connected to said vertical force members for vertically clamping said test specimen and for receiving the rotational and linear movement of said vertical loading assemblies and transferring the movement as vertical and shear loading to said test specimen.

2. The triaxial testing system of claim 1, said apparatus further comprising:
   a plurality of loading bars, each loading bar connected to one of said top and bottom joint assemblies and adapted for securing said vertical loading assembly; and
   a plurality of rods, each rod pivotably connected at opposing ends to said loading bars for receiving and transferring the rotational and linear movement of said loading bars to pivot to load said test specimen by said vertical loading assembly and said vertical clamping assemblies.

3. The triaxial testing system of claim 2, wherein said testing specimen further includes a plurality of horizontal and vertical ends that are shaped for clamping by said horizontal and vertical clamping assemblies.

4. The triaxial testing system of claim 2, wherein said testing specimen further includes at least one load measurement device for measuring axial and shear loads imparted to said testing specimen by said horizontal and vertical loading assemblies.

5. The triaxial testing system of claim 3, wherein said testing specimen further includes a plurality of rigid plates, each of said rigid plates disposed over one of said horizontal ends for spatially stabilizing said test specimen.

6. The triaxial testing system of claim 1, further including at least one crosshead connected to at least one of said top and bottom joint assemblies for imparting rotational and linear movement to said top and bottom joint assemblies.

7. A method of testing material properties of a test specimen, said method comprising the steps of:
   providing a triaxial testing apparatus with a top and a bottom joint assembly; a plurality of horizontal force members having first and second ends, each of said horizontal force members connected at the first end to one of said joint assemblies; a plurality of horizontal loading assemblies, each of said horizontal loading assemblies connected to the second end of at least one of said horizontal force members, a plurality of horizontal clamping assemblies connected to said horizontal loading assemblies at an end opposite of said horizontal loading assemblies connected to said horizontal force members, a plurality of vertical force members connected to a sleeve of each of said top and bottom joint assemblies; and a plurality of vertical loading assemblies connected to said vertical force members, a plurality of vertical clamping assemblies connected to said vertical loading assemblies at an end opposite of said vertical loading assemblies connected to said vertical force members;

clamping the test specimen with said horizontal clamping assemblies and with said vertical clamping assemblies;

imparting rotational and linear movement to said top and bottom joint assemblies;

receiving the rotational and linear motion from said top and bottom joint assemblies to horizontal loading assemblies and to said vertical loading assemblies and onto said horizontal clamping assemblies and said vertical clamping assemblies;

transferring the rotational and linear motion by said horizontal clamping assemblies as multi-axial and shear loads to the test specimen; and transferring the rotational and linear motion by said vertical clamping assemblies as vertical and shear loading to the test specimen.

8. The method of claim 7, further comprising a step of shaping the ends of the test specimen for clamping.

9. The method of claim 7, further comprising a step of measuring the vertical, multi-axial and shear loads and strains imparted to the test specimen.

10. The method of claim 7, further comprising a step of connecting at least one crosshead to at least one of said top and bottom joint assemblies to thereby impart rotational and linear movement to said top and bottom joint assemblies.

11. An apparatus for the triaxial testing of material properties of a test specimen, said apparatus comprising:

a top and a bottom joint assembly, each of said assemblies having sleeves capable of rotational movement about and linear movement along a longitudinal axis;

a plurality of horizontal force members having first and second ends, each of said horizontal force members connected at the first end to one of said joint assemblies for receiving the rotational and linear movement of said top and bottom joint assemblies;

a plurality of horizontal loading assemblies, each of said horizontal loading assemblies connected to the second end of at least one of said horizontal force members for receiving the rotational and linear movement of said horizontal force members;

a plurality of horizontal clamping assemblies, each of said horizontal clamping assemblies connected to said horizontal loading assemblies at an end opposite of said horizontal loading assemblies connected to said horizontal force members, for horizontally clamping the test specimen and for receiving the rotational and linear movement of said horizontal loading assemblies and transferring the movement as multi-axial and shear loading to the test specimen;

a plurality of vertical force members connected to a sleeve of each of said top and bottom joint assemblies for receiving the rotational and linear movement of said top and bottom joint assemblies;

a plurality of vertical loading assemblies connected to said vertical force members for receiving the rotational and linear movement of said vertical force members; and a plurality of vertical clamping assemblies, each of said vertical clamping assemblies connected to one of said vertical loading assemblies at an end opposite of said vertical loading assemblies connected to said vertical force members for vertically clamping the test specimen and for receiving the rotational and linear movement of said vertical loading assemblies and transferring the movement as vertical and shear loading to the test specimen.

12. The apparatus of claim 11, wherein said vertical force members further comprise:

a plurality of loading bars, each loading bar connected to one of said top and bottom joint assemblies and adapted for securing said vertical loading assembly; and a plurality of rods, each rod pivotably connected at opposing ends to said loading bars for receiving and transferring the rotational and linear movement of said loading bars to pivot to loading the test specimen by said vertical loading assembly and said vertical clamping assemblies.

* * * * *